United States Patent [19]

Pao

[11] Patent Number: 4,476,862

[45] Date of Patent: Oct. 16, 1984

[54] METHOD OF SCLERAL MARKING

[76] Inventor: David S. C. Pao, 95 High Point Dr., Churchville, Pa. 18966

[21] Appl. No.: 428,849

[22] Filed: Sep. 30, 1982

Related U.S. Application Data

[60] Division of Ser. No. 213,861, Dec. 8, 1980, abandoned, which is a continuation of Ser. No. 9,422, Feb. 5, 1979, abandoned.

[51] Int. Cl.³ ............................................. A61B 17/39
[52] U.S. Cl. ................................................ 128/303.17
[58] Field of Search ...................... 128/303.13, 303.14, 128/303.17, 303.18, 303.19, 800

[56] References Cited

U.S. PATENT DOCUMENTS

| | | | |
|---|---|---|---|
| 1,814,791 | 7/1931 | Ende | 128/303.17 |
| 1,983,669 | 12/1934 | Kimble | 128/303.17 |
| 2,275,167 | 3/1942 | Bierman | 128/303.17 |
| 3,651,812 | 3/1972 | Samuels | 128/303.18 |
| 3,920,021 | 11/1975 | Hiltebrandt | 128/303.17 |
| 3,987,795 | 10/1976 | Mornson | 128/303.14 |
| 4,034,762 | 7/1977 | Casens et al. | 128/303.17 |
| 4,103,688 | 8/1978 | Edwards | 128/303.17 |

OTHER PUBLICATIONS

"Bipolar Forceps for Electrocautery Tonsillectomy", Reed et al., Transaction of AAOO, vol. 78, (1974).
"Bipolar Coagulation in Ophthalmic Operations", McPherson, Jr. Amer. Journ. of Ophthamology, vol. 73, No. 5, May (1972).
Decker et al., "An Electrocautery Instrument . . . ", 10th Annual Rockey Mountain Bio. Eng. Symposium, Boulder, Col., May 7-9, 1973, pp. 5-10.
Schmidt et al., "Vas Cautery . . . " Urology, vol. III, No. 5, May, 1974, pp. 604-605.

*Primary Examiner*—Lee S. Cohen
*Attorney, Agent, or Firm*—Woodcock Washburn Kurtz Mackiewicz & Norris

[57] ABSTRACT

An electrode for use in electrocautery includes a central electrode having an outer electrode coaxially disposed therearound. The central and outer electrodes are electrically insulated from each other and are adapted to receive a high frequency voltage or direct voltage thereacross. The diameter of the central electrode as well as the inner and outer diameters of the outer electrode are dimensioned in accordance with the designated use of the probe, for example: general surgery, specialty surgery or micro surgery. In the preferred embodiment, the central or axial electrode has an elongate cylindrical shape with one end thereof tapering down to a point. The outer electrode has an elongate hollow tubular shape which is coaxially disposed around the central electrode. A first end of the outer electrode is disposed slightly behind the tapered tip of the central electrode in order to form a probe end wherein the tapered tip of the central electrode protrudes slightly beyond the plane defining the terminus of the outer electrode, depending on its use the tip need not be tapered nor protrude. Depending upon the use, the probe end may be either straight or curved. The electrodes are incorporated into an insulated holder which includes an electrical connector for mating to a high frequency voltage source.

1 Claim, 7 Drawing Figures

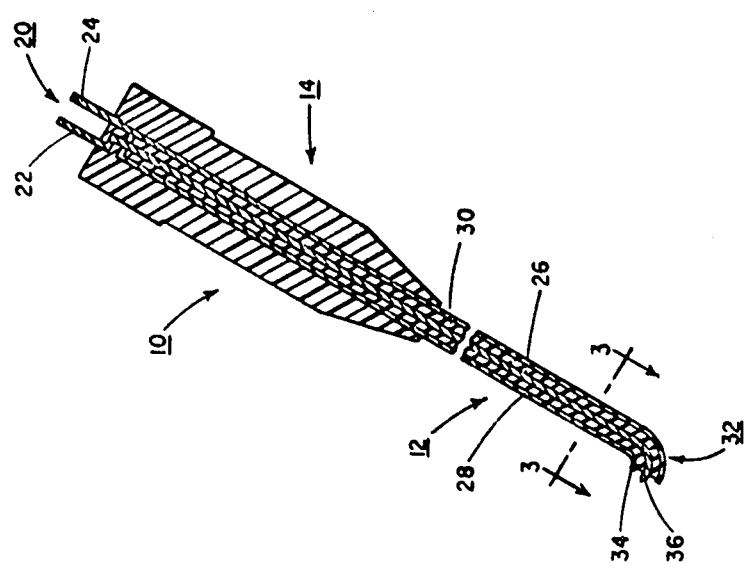
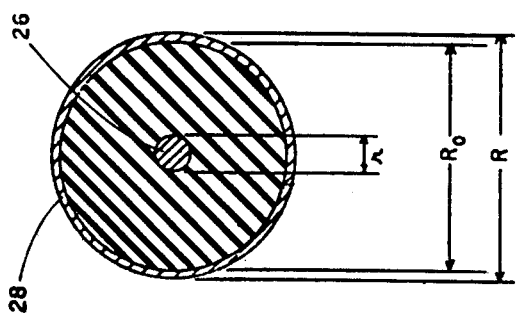
Fig.2
Fig.3

METHOD OF SCLERAL MARKING

This is a division of application Ser. No. 213,861, filed Dec. 8, 1980, now abandoned, which in turn is a continuation of Ser. No. 9,422 filed Feb. 5, 1979, now abandoned.

BACKGROUND OF THE INVENTION

This invention relates to electrosurgical devices and in particular to a probe for use in performing electrocautery and ophthalmic operations.

Electricity has been used to cauterize tissue in essentially two different ways. One technique comprises the use of an electrical current to heat a resistance element, the heated element then being applied to the tissue to be cauterized. The use of this technique precludes the necessity of applying an electrical current through the tissue. The other technique comprises the application of an alternating current through the tissue which causes cauterization in the vicinity of the electrode tip due to the high current density in this region.

Heretofore, the application of alternating current through the tissue was usually performed by using either a unipolar or bipolar technique. In the unipolar technique, the patient is placed on a ground plate which forms one electrode. The other electrode comprises a probe disposed in an insulated hand piece. The ground plate and the probe are electrically connected across the terminals of a high frequency voltage source. Using this technique, the tip of the probe is applied to the tissue. The current flows between the probe and the ground plate, with cauterization occurring in the vicinity of the probe tip due to the high current density in this region. This technique has several disadvantages, among which are the possibility of ground plate burn and cross-cardiac conduction difficulties due to the face that the current is flowing between the probe and the ground plate through the patient's body. In addition, this technique requires that the tissue area be relatively dry and uniform in order to obtain repeatable results without having to constantly adjust the output of the high frequency power supply.

The other technique involves the use of bipolar forceps as an electrosurgical instrument. Using this instrument, the destructive effects are passed between two points in the field, each blade of the forceps constituting one electrode. This instrument can be used in a wet field, and since current passes from one blade to the other, only that tissue grasped in the forceps will be coagulated and the spread of coagulation to adjacent tissue is prevented. Bipolar forceps have been used for electrocautery in tonsillectomies (See article entitled "Bipolar Forceps for Electrocautery Tonsillectomy", Reed, et al, Transactions of AAOO, Vol. 78, 1974) and has also been used in ophthalmic applications (See "Bipolar Coagulation In Ophthalmic Operations, McPherson, Jr., American Journal of Ophthamology, Vol. 73, No. 5, May 1972). In the bipolar application, the distance between the tips are variable in most cases, therefore there is variable coagulation with the same setting of the power supply. There are also forceps in which the distance between the tips is fixed. However, although the coagulation is more uniform when this type of forcep is used, the result is a linear or line coagulation or a smudge. Such linear coagulation or smudge is undesirable in microsurgery or scleral marking.

SUMMARY OF THE INVENTION

In order to overcome those problems attendant with unipolar and bipolar forceps techiques for electrocautery, applicant's invention discloses an apparatus for precisely limiting the cautery to a predetermined area in either a wet or dry field. The apparatus comprises an elongate cylindrical axial electrode having a first end which forms a portion of the probe region. A hollow tubular outer electrode, which is electrically insulated from the axial electrode, is coaxially disposed around the axial electrode. The outer electrode has a first end which also forms a portion of the probe region of the apparatus. The first end of the axial electrode protrudes slightly beyond the first end of the outer electrode. The outer and axial electrodes are adapted for electrical connection to high frequency power supply from which a high frequency voltage is applied between the axial and outer electrodes.

The probe region, with the high frequency voltage applied across the electrodes thereof, is placed in contact with the tissue area to be cauterized. When contact is made, the electrical current flows in a radial direction between the axial electrode and the coaxial outer electrode. The current density is inversely proportional to the square of the distance from the axial electrode to the coaxial outer electrode. Consequently, the area of cauterization will be substantially circular having a diameter which is proportional to the voltage applied between the electrodes. Consequently, the use of this apparatus will provide spot cauterization having a well defined area. In addition, since a bipolar technique is employed, electric current will not flow through the patient's body thereby negating the possibility of concomitant adverse side effects.

Accordingly, it is an object of the present invention to provide a novel bipolar electrode probe for electrocautery capable of greater pinpoint accuracy in microsurgery and scleral operations.

It is a further object of this invention to provide an apparatus for producing cautery spots of predetermined areas.

Another object of the present invention is to provide an apparatus which produces spot cauterization without passing a current through the patients body.

It is a further object of the present invention to provide an apparatus for producing repeatable marks for use in procedures such as scleral marking.

These and other objects of my invention will become apparent from the following description with reference to the accompanying drawings.

BRIEF DESCRIPTION OF THE DRAWINGS

FIG. 2 is a cross section taken along lines 2—2 of FIG. 1.

FIG. 3 is a cross section taken along lines 3—3 of FIG. 2.

DETAILED DESCRIPTION OF THE DRAWINGS

Figure 1:
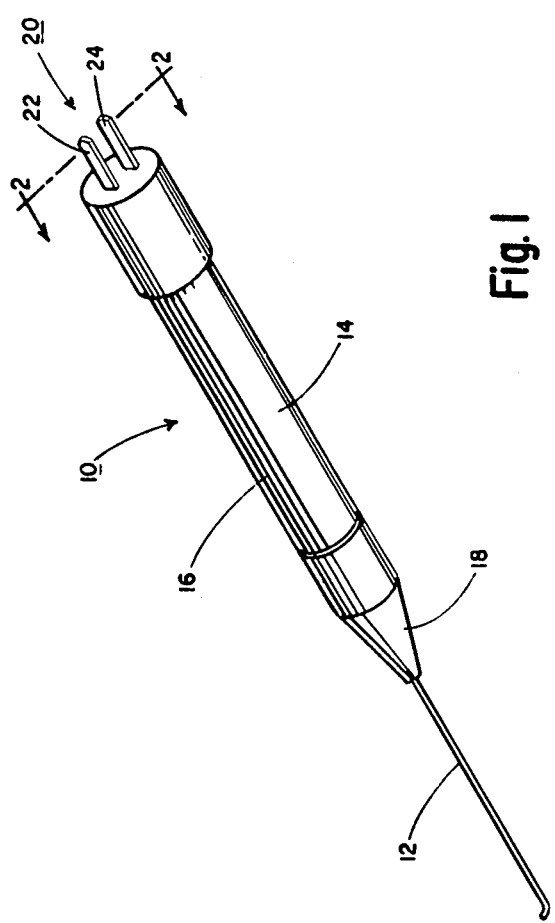
FIG. 1 is an isometric view of a preferred embodiment of the coaxial bipolar probe of the present invention.
Figure 5:
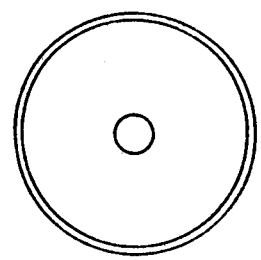
FIG. 5 is an end view of the terminal or probe region shown in FIG. 4.

In FIG. 1 there is shown a preferred embodiment of the coaxial bipolar probe of the present invention designated generally 10. The probe 10 includes an electrode portion 12 disposed in a handpiece portion 14. In the preferred embodiment, the handpiece portion 14 is made of an electrically insulating polymeric material, such as teflon (polytetrafluorethylene) or polysulphone, configured in a pencil-shaped form having a cylindrical body region 16 and a tapered forward region 18. Although a pencil-shaped configuration is preferred, it should be noted that any configuration of the handpiece portion 14 which is easily, comfortably, and conveniently grasped in the hand will also be suitable and is considered within the scope and contemplation of my invention. The end of the handpiece portion 14, remote from the tapered portion 18, includes an electrical connection portion designated generally 20. The electrical connection portion 20, preferably comprises a pair of electrically conductive pins 22 and 24 adapted for making in a female receptacle (not shown). The female receptacle is in turn electrically connected to the output of a high frequency power supply, for example a standard electrosurgical power unit with reduced power and bipolar output, such as manufactured by Codman-Mentor, MIRA (Medical Instrument Research Associates), or Valley Lab. When inserted in the female connector, the pins are therefore electrically connected to the output of the high frequency power supply.

Referring now to FIG. 2, there is shown a cross section of the preferred embodiment of the coaxial bipolar probe shown in FIG. 1. As shown in FIG. 2, the electrode portion 12 comprises an elongate cylindrical axial or central electrode 26 and an elongate, hollow tubular outer electrode 28 which is coaxially disposed around the inner electrode 26. The inner and outer electrodes are made of an electrically conductive material, preferably stainless steel or other corrosive resistant conductor. The coaxial relationship and spacing between the axial and outer electrodes is maintained by inserting an electrically insulating polymeric material 30 therebetween, such as teflon or polysulphone the preferred embodiment.

Figure 4:
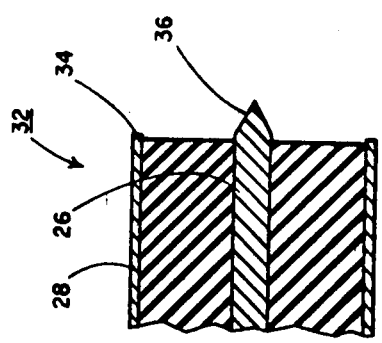
FIG. 4 is a cross section of a terminal or probe region of the coaxial bipolar probe of the present invention.

One end of the electrode portion 12 comprises a probe region designated generally 32 (see FIGS. 2 and 4). The probe region 32 includes a first end 34 of the outer conductor 28 and a first end 36 of the axial conductor 26. In the preferred embodiment, the first end 36 of the axial conductor 26 protrudes slightly beyond the first end 34 of the outer conductor 28 in order to effectuate good tissue contact. In the embodiment shown in FIGS. 2 and 4, the first end 36 of the axial conductor 26 is tapered down to a point the taper beginning at about the first end 34 of the outer electrode 28. It should be noted that the first end 36 may terminate in a sharp point, a dull point, or have no taper whatsoever depending upon current density characteristics desired. Consequently, all of these first end configurations are considered to be within the scope and contemplation of my invention. It should also be noted that the probe region as shown in FIG. 2, is curved through approximately 90 degrees. This type of curve may be suitable for a specific application. However, a straight probe may be more suitable for another application and probed regions having curved portions to meet other specific applications are considered to fall within the scope and contemplation of my invention.

The ends of the axial and outer electrodes remote from the probe region 32 are electrically connected to the pins 22 and 24 respectively. Consequently, when the pins are connected to the mating female connector which is in turn electrically connected to the power supply, and the power supply is energized, the high frequency voltage output from the power supply will appear between the axial electrode 26 and the outer electrode 28.

The preferred dimensions of the electrodes, at least in the probe region 32, are hereinafter discussed in conjunction with FIG. 3. As shown in FIG. 3, the axial electrode 26 has a cross sectional diameter designated r. The inner diameter of the outer electrode 28 is designated $R_0$ and the outer diameter is designated R. The dimensions r, $R_0$ and R have variable sizes depending upon the use of the probe, for example whether used in general surgery, specialty surgery, or in micro-surgery. For use in general and non-microsurgery, the preferred ranges are: r = 1.0 mm–10.0 mm; R, $R_0$ = 2 mm–30 mm; and R–$R_0$ 0.5 mm–1.0 mm. For use in microsurgery, the preferred dimensions are: r = 0.1 mm–1.0 mm (note that if required, the tip of the axial electrode 26 may be tapered to a point having a diameter which is smaller than 0.1 mm); R, $R_0$ = 0.5 mm; and R–$R_0$ 0.1 mm–2 mm. The preferred prototype embodiment of the apparatus for micro surgery applications has the following dimensions: r–0.5 m, R = 2.5 mm, and $R_0$ = 2.0 mm. The preferred prototype embodiment for use in general and non-micro surgical applications has the following dimensions: r = 1.0 mm, R = 3.0 mm, R = 3.5 mm, The coaxial bipolar probe of the present invention is used as follows. The power supply is electrically connected to the axial 26 and outer 28 electrodes of the coaxial bipolar probe 10 by means of a female connector mated to the connector pin 22 and 24. The power supply is then energized causing the high frequency voltage output to appear between the axial 26 and outer 28 electrodes. Note this energization can occur before and after the probe contacts the tissue as desired. The end of the probe region 32 is placed against the tissue causing the ends 36 and 34 of the axial 26 and outer electrodes 28 respectively to come into contact with the tissue. Electrical current then flows through the tissue between the axial 26 and outer 28 electrodes.

The current density is greatest at the tip of the axial electrode 26 and decreases in proportion to the square of the radius in the radial direction toward the outer electrode 28. This is shown schematically in FIG. 5a where the arrows 38 extend radially from the axial conductor 26 toward the coaxial outer conductor 28. As previously stated, the current density is highest in the vicinity of the axial conductor 26 and decreases in proportion to the square of the radial distance from the axial conductor 26 toward the outer conductor 28.

Figure 5B:
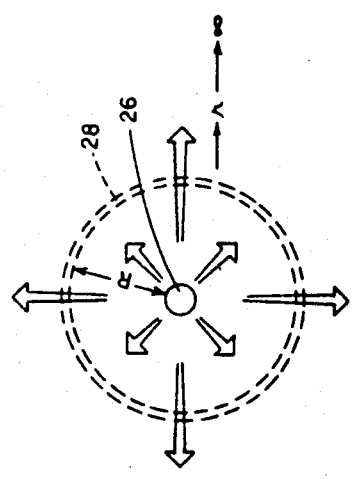
FIGS. 5a and 5b are schematic representations of current density obtained in a coaxial bipolar probe, FIG. 5a showing the case where the outer coaxial conductor is displaced a finite distance from the axial conductor and FIG. 5b showing the special case where the distance between the coaxial outer conductor and the axial inner conductor is infinite.
Figure 5A:
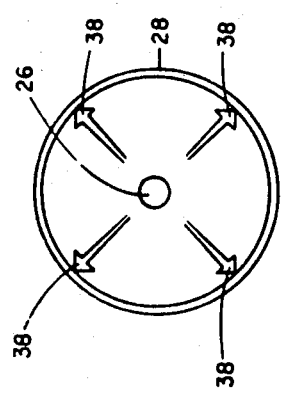

FIG. 5b depicts the special case where the coaxial outer conductor 28 is displaced from the axial inner conductor 26 by a radial distance equal to infinity. This special case approximates that of the unipolar probe wherein the unipolar probe would correspond to the axial conductor 26 and the ground plate corresponds to the outer conductor 28 located at a radial distance which is infinite from the axial conductor 26. In FIG. 5b, the outer conductor 28 is represented by dotted lines to indicate that it is located at a very great distance (approximating infinity) from the axial conductor 26. In the case illustrated in FIG. 5b, the current density is still highest in the vicinity of the axial conductor, or unipolar probe 26, and decreases in proportion to the square of the radial distance away from the axial conductor 26. Note that in this special case, the area of cautery will still approximate a spot since the current density will decrease in substantially radially symetrical fashion to a point where tissue coagulation or cauterization will no longer occur.

As previously stated, this uniform or radially symmetric decrease in current density could be assumed only when working in a substantially dry field. When using a coaxial probe of the present invention, wherein the coaxial outer conductor is at a finite radial distance from the axial conductor, the uniformity or spot cauterization effect is enhanced. Consequently, a coaxial bipolar probe in accordance with the present invention can be introduced to provide precise spot coagulation. In addition, the configuration of the probe of the present invention enables the achievement of spot coagulation without a charring effect since relatively low power, preferably in the range of 1-15 watts is used. The applied power is variable depending on micro or non-micro surgery is use. Note however that if a charring effect under control is desired, as for example in tissue marking such as scleral marking, an increase in the power applied produces good repeatable marks. In addition, spot accuracy, such as provided by the probe of the present invention, allows the probe to coagulate in areas without shrinking the tissue. For example, it was found that one can control the heating effect so well that it was possible to coagulate small vessels in the limbus region of the eye without shrinking tissue in that area as occurs when using bipolar forceps.

It will be understood that various changes in the details, materials and arrangement of parts which have been herein described and illustrated in order to explain the nature of this invention may be made by those skilled in the art within the principle and scope of the invention as expressed in the following claims.

I claim:

1. A method of scleral marking comprising the steps of:
   (a) providing a hand held apparatus comprising an elongate cylindrical axial electrode having a first end, a tubular outer electrode coaxially disposed around and electrically insulated from said axial electrode, and wherein said first end of said axial electrode extends beyond an end of said outer electrode and is tapered to a point, said taper beginning at about the end of said outer electrode;
   (b) providing means electrically connected to said hand held apparatus for applying an electrical power source across said axial and outer electrodes; and
   (c) activating said electrical power source while touching said tapered point and the end of said outer electrode to the sclera to produce repeatable marks on the sclera.

* * * * *